United States Patent [19]

Leslie et al.

[11] Patent Number: 4,654,209

[45] Date of Patent: Mar. 31, 1987

[54] PREPARATION FOR PERCUTANEOUS ADMINISTRATION

[75] Inventors: Stewart T. Leslie; Alan Rhodes, both of Aberdeen, Scotland; Cyril Boroda, London, England; Alfred Halpern, Great Neck, N.Y.

[73] Assignee: Euroceltique, S.A., Luxembourg, Luxembourg

[21] Appl. No.: 765,451

[22] Filed: Aug. 14, 1985

Related U.S. Application Data

[60] Continuation of Ser. No. 587,505, Mar. 8, 1984, abandoned, which is a continuation of Ser. No. 309,042, Sep. 18, 1981, abandoned, which is a division of Ser. No. 203,481, Nov. 3, 1980, Pat. No. 4,322,433.

[30] Foreign Application Priority Data

Nov. 6, 1979 [GB] United Kingdom .................. 793830

[51] Int. Cl.⁴ ............................................. A61K 31/79
[52] U.S. Cl. ........................................ 424/80; 514/41; 514/152; 514/159; 514/162; 514/165; 514/166; 514/179; 514/223; 514/263; 514/352; 514/357; 514/400; 514/404; 514/462; 514/628; 514/635; 514/742; 514/947
[58] Field of Search ................ 514/742, 162, 41, 152, 514/159, 165, 166, 179, 223, 263, 352, 357, 400, 404, 462, 628, 635, 947; 424/80

[56] References Cited

U.S. PATENT DOCUMENTS

| | | | |
|---|---|---|---|
| 3,395,215 | 7/1968 | Schubert | 424/273 |
| 3,551,554 | 12/1970 | Herschler | 424/7 |
| 3,609,102 | 9/1971 | Schussman | 424/343 |
| 3,789,119 | 1/1974 | Fosari et al. | 424/298 |
| 4,197,318 | 4/1980 | Sipos | 424/243 |
| 4,322,433 | 3/1982 | Leslie et al. | 424/243 |
| 4,323,577 | 4/1982 | Ohkuna et al. | 424/298 |

OTHER PUBLICATIONS

Lachman et al–The Theory & Practice of Industrial Pharmacy, 2nd ed. (1976), pp. 215–244.

Kremers-Urban–"Nitrol" Ointment, package insert, 10/77, p. 1200.

*Primary Examiner*—Leonard Schenkman
*Attorney, Agent, or Firm*—Steinberg & Raskin

[57] ABSTRACT

A preparation for percutaneous administration of nitroglycerine, said preparation comprising nitroglycerine incorporated in a cream base in an amount not less than about 0.05% by weight based on the total weight of the preparation. The composition may also contain other medicaments, the bioavailability of which is enhanced by the nitroglycerine. The action of the preparation against for example angina may be brought about by having an appropriate amount of nitroglycerine or as additional medicament another medicament active against angina. The preparation may contain an hydroxyalkylcellulose which may provide, in combination with a waxy component in the cream, for example a higher aliphatic alcohol, a prolonged release effect. The preparation has advantages particularly as regards bioavailability over prior uniphasic ointments.

22 Claims, No Drawings

PREPARATION FOR PERCUTANEOUS ADMINISTRATION

This is a continuation of Ser. No. 587,505, filed Mar. 8, 1984, now abandoned, which in turn is a continuation of Ser. No. 309,042 filed Sept. 18, 1981, now abandoned, which is in turn a divisional of Ser. No. 203,481, filed Nov. 3, 1980, now U.S. Pat. No. 4,322,433.

BACKGROUND OF THE INVENTION

The transdermal route of administration of pharmacologically active substances has been generally limited to those substances intended solely for localized action and only rarely has this route been used to obtain a systemic effect. Thus we find that the teachings of the prior art establish that the transdermal route of drug administration results in variable and ineffective blood levels for virtually all pharmacologically acitve substances with only a range exception as for example nitroglycerine being administered transdermally. However, when nitroglycerine is used transdermally it is dispersed in high concentrations (20 milligrams per gram) in single phase lipophilic ointments because the limitations of these unctious preparations materially restrict their use and consequent physicologic effects.

Prior art nitroglycerine ointments are all single lipophilic systems comprisng a non-polar fatty base which contrasts sharply with the complex polar composition of skin and skin secretions. The opposing properties between skin and fatty ointments result in an irregular interface contact between the topically applied single phase lipophilic ointment composition and the hydrophilic skin. The single phase lipophilic ointment tends to form an occlusive film on the skin surface which facilitates pooling of the essentially aqueous polar skin fluids to cause a discontinuity of the interface between the skin and applied ointment. The consequent irregular and variable absorption pattern diminishes the bioavailability of the active substance to render the single phase lipophilic bases generally ineffective for percutaneous administration.

To overcome the irregular absorption pattern and poor bioavailability observed with the older single phase nitroglycerine fatty ointments, greatly increasing concentrations of active ingredient have been used to force penetration to take place. This increased quantity of drug added a noxious and toxic threat to the patient because of its potency as well as burdening an already inferior dosage form with limited absorption. These limitations are readily seen when a comparison is made of the varying concentrations of nitroglycerine required for clinical use by the different routes of administration. For example, 0.15 mg/tablet is utilized for oral administration, and 0.60 mg/tablet is utilized for sublingual administration, but when nitroglycerine is administered topically in the single phase lipophilic ointment, then twenty (20) milligrams per gram are required to achieve comparable bioavailability.

The amount of nitroglycerine required to achieve the desired result percutaneously from a lipophilic ointment base is from 33 to 133 times the amount of nitroglycerine required to achieve the same affect by the sublingual and/or oral routes of administration for the same substance.

The single phase lipophilic bases of the nitroglycerine ointments of the prior art generally consist of lanolin, or lanolin and white petrolactum mixtures. These preparations are unctious, fatty substances so that a sticky, greasy layer remains on the skin for some time after administration and stains clothes and other linens. Moreover, it is known that lanolin elicits an allergic response in some individuals (about 1%) and this is a further disadvantage to the use of the prior art ointments.

Nitroglycerine is a volatile explosive compound and is available as an article of commerce as an adsorbate on diverse carriers including glycose substance and inert mineral carriers.

Furthermore, the lactose which comprises a necessary adsorbate ingredient when nitroglycerine is used in pharmaceutical compounding, is not soluble in the single phase lipophilic systems and therefore the finished unctious ointment preparation is gritty in both texture and appearance.

SUMMARY OF THE INVENTION

We have now found that the disadvantages associated with the prior art ointments may be largely overcome by the use of creams as described in more detail below. We have also surprisingly found that in using such creams the nitroglycerine acts in such a manner as to facilitate the passage of other medicaments through the skin and thus increases their bioavailability at the site of action. Also it has been found that advantages derive from the use of an hydroxyalkyl cellulose in the preparation of the cream particularly where the cream contains a higher aliphatic alcohol as one of its constituents, in particular in producing a cream which has a controlled slow release effect, as more fully described below.

Broadly therefore the invention provides a medicinal preparation adapted for topical application comprising nitroglycerine distributed in a cream base which is a biphasic lipophilic/hydrophilic emulsion the lipophilic phase constituting the internal phase and the hydrophilic phase constituting the external phase.

The amount of nitroglycerine present depends on the action desired from the preparation; thus it the action is that an anti-angina preparation the nitroglycerine concentration should be greater than that where the preparation is merely used to increase the bioavailability of another or other medicament(s) present in the composition acting against angina or other conditions. This aspect of the invention is described more fully below.

In the production of the nitroglycerine-containing creams according to the invention, the lipophilic phase may contain or consist of a higher aliphatic alcohol, by which we mean an aliphatic alcohol containing from 8 to 18 carbon atoms which may be substituted by a further aliphatic group containing from 8 to 18 carbon atoms. As an example of such aliphatic alcohol, cetyl alcohol may be mentioned. As an example of a substituted aliphatic alcohol, cetostearyl alcohol may be mentioned. Other alcohols include lauryl alcohol, myristyl alcohol and stearyl alcohol.

It has been found that the use of an hydroxylalkyl cellulose in the production of the cream in combination with the higher aliphatic alcohol, as described below, leads to particular advantages as regards controlled release of the medicament. The alkyl fragment of the hydroxyalkyl cellulose preferably contains 1 to 4 carbon atoms. Specifically hydroxymethyl cellulose, hydroxyethyl cellulose and hydroxypropyl cellulose are preferred.

This invention therefore relates to a novel pharmaceutical preparation containing 2,4,6-trinitroglycerine (hereinafter referred to for convenience as "nitroglycerine") distributed in a balanced biphasic hydrophilic-lipophilic composition. The novel pharmaceutical preparations of this invention facilitate the transdermal absorption of medicaments. A preferred use in particular for the novel pharmaceutical preparation is for the treatment of patients suffering from angina.

When the preparation of the invention contains a medicament other than nitroglycerine, or an amount of nitroglycerine in excess of a certain limit, a synergistic action takes place to result in a greatly improved percutaneous transport of said pharmacologically active substance or said excess nitroglycerine which is demonstrated through an improved bioavailability of the active compound. By bioavailability is meant the amount of the active substance available in the blood to exert its desired effect.

The factors which influence percutaneous absorption of pharmacologically active substances are complex bisphasic hydrophilic and lipophilic oriented physiologic and physical-chemical energy systems. Penetration of molecules into and through the epidermal tissues occurs in accord with Fisk's law which states that the rate of diffusion of a substance is proportional to the driving force. The driving force is defined as the difference between the concentration of molecules being transported from a base applied to the skin and the concentration of the same molecules in the skin. The direction of the driving force is from the greater concentrations to the lesser concentration until an equilibrium results.

The primary barrier to transdermal absorption arises in the epidermis which is the external surface of the skin and is composed of five cellular layers;

(1) Stratum corneum (horny layer)
(2) Stratum lucidum ("Barrier zone")
(3) Stratum granulosum (granular layer)
(4) Stratum malpighii (prickle cell layer)
(5) Stratum germinativum (basel cell layer)

The route of entry of medicaments into and through the skin is considered to be entirely via the epidermal tissue layers and the role of the skin appendages i.e., the hair follicles, sweat glands and sebaceous glands, is virtually nil. The skin appendages minimally enter into the transfer of non-polar medicaments from single phase unctuous ointments, since the physiology of the hair follicle and sebaceous gland is lipophilic oriented.

These appendages represent a potential low-level parallel route to the epidermal tissues for certain lipophilic substances i.e., nitroglycerine, from a fatty, unctuous carrier. However, there are many reasons to establish that this lipophilic route is insignificant as a transdermal pathway and when utilized requires large wasteful excesses of active material to accomplish transdermal penetration.

The role of the hair follicle in the contribution to the proportion of the amount of a substance absorbed through the skin was demonstrated with pig-skin. It was shown that tri-n-butyl-phosphate exhibits the same level of percutaneous absorption whether or not the area includes hair follicles. This demonstrates that the contribution of the hair follicle to transdermal transfer is insignificant.

The lipid orientation of the sebaceous gland secretions in and around the hair follicles, suggest this pathway to be a route for medicaments from single phase lipophilic ointments. It is now established that the sebaceous glands located in the skin and emptying into the hair follicle canal do not play any significant role in the percutaneous absorption of medicaments.

Studies of the mechanism of absorption of substances in and through the skin have similarlly established that the sweat glands to not enter into the percutaneous transfer of materials. There are three times as many sweat glands per unti area of palmar skin and soles of the feet as in other tissues, yet the skin of the palm and the sole is less permeable to the penetration of medicaments than is any other portion of the body and this area is virtually disregarded as a site for percutaneous administration. The epidermis principally controls transdermal absorption and the stratum corneum and stratum lucidum cell layers are the major route for transdermal penetration.

The stratum corneum of the epidermal tissue is a horny, cellular layer made up of keratinized cells, and accounts for almost all of the transfer barrier function of skin. The penetration of substances applied to the skin surface is inversely related to the thickness of the stratum corneum layer. When active substances penetrate into the epidermis, these substances concentrate initially in the stratum corneum to form a barrier-reservoir which limits further penetration through equilibrium formation. Meanwhile, the cellular biochemistry degrades the active agents present in the tissue barrier-reservoir to vitiate their pharmacologic activity.

The stratum lucidum is a thin membrane-like cell layer primarily serving to block the transport of water and polar substances across the skin. The stratum lucidum forms a second formidable aqueous-barrier against most substances applied to the skin. A leeching action of the reservoir-barrier of the stratum corneum brings molecules dissolved in the biologic fluids to the stratum lucidum and a new reservoir-barrier is created. This second reservoir-barrier retains the active substances until these are transported by tissue fluids to the blood vessels and the lymphatic system, to enter the circulation.

As the circulation depletes the stratum lucidum barrier-reservior of its active substance, the lowered concentration induces the transfer of the same active substance from greater concentration present in the barrier-reservoir of the stratum corneum. As the stratum corneum barrier-reservoir becomes depleted, diffusion of the respective molecules from the topically applied carrier across the continuous skin-cream interface occurs to replenish the respective epidermal barrier-reservoirs, to begin the cycle once again.

This transport cycle continues as long as the percutaneous driving force directs the flow or until the applied topical preparation is depleted of the desired active substance intended for percutaneous administration, or until the skin-vehicle interface contact is destroyed.

As far as is known, the only substance administered percutaneously for a systemic effect is nitroglycerine in single phase lipophilic ointments. As stated above it has been found that the disadvantages of these prior art lipophilic ointment-based preparations for topical application can be reduced and even substantially avoided by the pharmaceutical preparations of the present invention in which the carrier is a balanced hydrophilic-lipophilic cream preparation and not a single phase lipophilic ointment and at the same time providing a synergistic local stimulant action to the circulation, thereby increasing the driving forces.

The hitherto unknown desirable properties of the new preparations of the present invention arise from the critical hydrophilic-lipophilic balance of the vehicle. This balance enables the optimal rapid diffusion of the pharmacologically active substances from the carrier into the epidermal tissues to achieve a continuous dynamic penetration to the respective barrier-reservoirs. The synergistic local vasodilation stimulates the circulation of the epidermis thereby facilitating the rapid transport of the molecules from the respective epidermal barrier-reservoirs into the blood.

Because of the critical biphasic hydrophilic-lipophilic balance of the new vehicle, the continuous uniform interface formed between skin and vehicle is not interrupted as in the older single phase systems and permits the continuing transport of the active substance from the base to the circulation until an applied dose is exhausted. This new balanced system avoids the wastage of active substances of the older fatty ointments and achieves a desirable bioavailability with greatly reduced quantities of active ingredients than is required for the older single phase lipophilic systems. This results in a greater therapeutic efficacy and increased safety for this route of administration.

The new preparation intended for improved percutaneous transport of a pharmacologically active substance comprise:

(1) a hydrophilic component of strong to medium polarity, e.g., water, propylene glycol and/or glycerine, which is in critical proportion to;

(2) a lipophilic component, e.g., one including a higher aliphatic alcohol as defined above, if desired together with fatty acid esters of a higher alcohol e.g., oleic acid decyl ester;

(3) a mixture of emulsifiers to provide a critical HLB (hydrophilic/lipophilic balance) value ranging from 8 to 14, with a preferred HLB value of 12, and, (4) nitroglycerine, in an amount of at least 0.05% by weight, the exact amount depending on the therapeutic purpose of the particular topical use and the nature of the pharmacologically active substance being transported as more fully described below.

In producing a composition according to the invention, the nitroglycerine is utilized in the form of the commercially available stabilized lactose adsorbate and is preferably dispersed in the lipophilic phase to extract the nitroglycerine from its stabilizing lactose substrate although this order of mixing is not critical. The whole is then mixed with water or other hydrophilic component to preferentially dissolve the lactose in the polar solvent (the hydrophilic phase) and the mixture is then emulsified into a cream.

According to a feature of the invention there is provided a process for the preparation of a composition according to the invention wherein nitroglycerine in the form of an absorbate is dispersed in a lipophilic phase including a higher aliphatic alcohol containing 8 to 18 carbon atoms which may be substituted by a further aliphatic group containing 8 to 18 carbon atoms, to extract the nitroglycerine from the adsorbate and the resulting lipophilic phase containing the nitroglycerine is mixed with a hydrophilic phase, the mixture subsequently being emulsified to provide a product of the desired HLB value.

According to another feature of the invention there may be present in the mixture forming the cream an hydroxyalkylcellulose, as defined above, so that a cream having a gel matrix is prepared. According to this aspect of the invention there is provided a process as defined above including the further step of incorporating in the cream an hydroxyalkylcellulose as defined above. The hydroxyalkylcellulose may be added to the cream-forming mixture prior to emulsion. The gel matrix emulsion cream system so produced provides the same bisphasic lipophilic/hydrophilic balance as the emulsion cream. In practice, the lipophilic components are warmed to approximately 80° C. to produce a homogeneous melt. Conveniently the emulsifiers are added to the molten lipophilic phase and then the nitroglycerine-lactose adsorbate is added. Water, preheated to approximately 80° C. is mixed with hydroxyalkylcellulose and added to the lipid phase. The mixture is allowed to cool with constant stirring to form a soft, white, homogeneous emulsion cream gel matrix.

The amount of hydroxyalkylcellulose component added in the biphasic emulsion cream to achieve the desired gel matrix formation is in critical proportion to the amount of lipophilic component used to form the emulsion cream. The critical ratio of from 1 part by weight of hydroxyalkylcellulose component for each 2 to 4 parts by weight of higher aliphatic alcohol in the lipophilic component used to prepare the emulsion cream is necessary to achieve the desired gel matrix formation.

The gel matrix emulsion system cream base may also be formed by adding the nitroglycerine to the polar hydrophilic fluid containing the hydroxyalkylcellulose to dissolve the lactose adsorbate and liberate nitroglycerine. The nitroglycerine is then stabilized by the hydroxyalkylcellulose component and the whole added to the molten lipophilic phase. The mixture is stirred while cooling to form the emulsion system gel matrix topical cream.

Appropriate pharmaceutical necessities, such as preservatives, diluents and aromatic coloring materials, may be added as these are required. Preservatives include esters of p-aminobenzoic acid.

The invention therefore provides a new pharmaceutical preparation as a topical vehicle comprising nitroglycerine distributed in a balanced biphasic lipophilic/hydrophilic cream base in the form of a biphasic emulsion cream which term includes a biphasic emulsion cream gel-matrix. By the term, 'cream' is meant the biphasic lipholic/hydrophilic emulsion system and in the 'creams' used according to the invention, the external phase is hydrophilic-polar whereas the internal phase is lipholic-non-polar. This system has an advantage in being compatible with epidermal chemistry to enable ready transfer of the active ingredient from the vehicle to the skin.

The precutaneous transfer of active substance from the base into the skin, takes place virtually completely so that a known amount of active ingredient as contained in the dose of preparation applied to the skin becomes bioavailable. The balanced hydrophilic/lipophilic vehicles do not form occlusive dressings on the skin and are easily spread to form a uniform film to cause intimate contact at the skin interface. Since these preparations are not greasy they do not stain clothing and linen. Through the use of the cream preparations of the present invention, the same order of drug transport is observed for both polar and non-polar active substances.

The nitroglycerine used in the manufacture of the preparation of the invention is the commercially available stabilized lactose adsorbate. Whether the nitroglycerine adsorbate is added to the lipophilic phase or the hydrophilic phase is not critical so long as the nitroglycerine is liberated into the lipophilic phase.

When heat is used to melt a waxy material prior to the incorporation of the nitroglycerine stabilized adsorbate such heat may be up to 80° C. It has surprisingly been found that the present process according to the invention is carried out without destruction or volatilization of the nitroglycerine during the emulsification phase utilized for the preparation of either the new biphasic emulsion cream or the emulsion gel matrix cream.

The amount of nitroglycerine present in the new topical preparations is at least 0.05% by weight and up to 1.5% by weight but preferably 0.25% by weight when the preparation is used as a vehicle for pharmacologically active substances. When molecules of larger size are transported these may require a higher concentration of nitroglycerine than those of smaller size. However, greater quantities of nitroglycerine may be required for therapeutic purposes, as for example in the treatment of angina. The exact amount of nitroglycerine to be used in the base depends upon the physical and chemical properties of the pharmacologically active substances intended for percutaneous administration together with the individual patient needs.

The optimal concentration range for nitroglycerine of from 0.05% to 0.25% by weight of the preparation, when the purpose of preparation is not primarily for the administration of the nitroglycerine, was established by means of plethysmography whereby it was found that when the concentration of nitroglycerine in the biphase emulsion cream and the biphase emulsion gel matrix cream of the invention is less than 0.05% by weight, it did not cause the necessary synergistic local vasodilation. The degree of local vasodilation caused by at least 0.05% of nitroglycerine increases when the greater amounts are used but reaches a steady state equilibrium when the concentration of nitroglycerine is 0.25% by weight. When greater amounts of nitroglycerine than 0.25% by weight are used, as for example, 0.5% by weight or larger, the local induced hyperemia acts to rapidly deplete the formed reservoir barriers of the epidermis and causes the adsorption of the nitroglycerine into the blood. This entry of the nitroglycerine into the circulation initiates a systemic action for the nitroglycerine which may or may not be desired, depending on the intended action.

The creams according to the invention are suitable for the treatment of patients suffering from angina and for this purpose, additional amounts of the pharmacologically active nitroglycerine are utilized to achieve the systemic cardiovascular effect. This action is different from the local synergistic circulatory stimulant function for nitroglycerine hitherto described.

It was found unexpectedly that the anginal patient may be satisfactorily treated by applying the preparation of the invention containing a preferred amount of nitroglycerine, e.g. 10% by weight, or an increase of 0.75% by weight of nitroglycerine over the 0.25% of nitroglycerine present in the carrier cream as the synergistic local stimulant. A group of 10 patients diagnosed as having variant angina associated with effort, were studied for the effects of different amounts of added nitroglycerine to the 0.25% by weight concentration of nitroglycerine already present in the biphasic cream vehicle of the invention. The following responses were reported after application of a 1 gram unit dose:

| Total Concentration of Nitroglycerine in Cream (% by weight) | No. of patients responding Effective | No response | Side-Effects |
|---|---|---|---|
| 0.25% | 0 | 10 | None |
| 0.50% | 2 | 8 | None |
| 0.75% | 5 | 5 | None |
| 1.00% | 9 | 1 | Headache (1) |
| 1.25% | 8 | 2 | Headache (2) |
| 1.50% | 10 | 0 | Headache (5) |
| 1.75% | 9 | 1 | Headache (6) |
| 2.00% | 8 | 2 | Headache (6) |

It will be seen that the steady state of adsorption of nitroglycerine from the cream of the present invention reaches equilibrium when the total concentration of nitroglycerine in the cream is about 1% by weight. When the concentration level of nitroglycerine is further increased, side-effects associated with overdosage, i.e., headache, begin to appear. Thus it will be observed that even at the 1% by weight total concentration of nitroglycerine, one patient complained of transitory headache but this number rapidly increased with added amounts of nitroglycerine. The significant improvement in the bioavailability of nitroglycerine from the cream of the invention takes place at about 1% by weight total concentration level when all impacting factors are considered.

These results establish that the range in effective total concentration of nitroglycerine in the preparation of the invention when used for the treatment of angina is greater than 0.75% by weight but less than 1.25% by weight, with a preferred total concentration of nitroglycerine in the vehicle of 1.0% by weight.

This observed effective dose range for transdermal administration of nitroglycerine to treat angina of from 0.75% to 1.25% by weight of nitroglycerine, with a preferred concentration of 1.0% by weight, represents a reduction of more than 100% in the amount of nitroglycerine required to treat angina by the transdermal route with the prior art fatty ointments and is a dramatic advance in the art. The magnitude of more than 100% reduction in the amount of active substance required to achieve an effective bioavailability of nitroglycerine when compared with the 2.0% by weight of nitroglycerine required by the older single phase ointments represents a material change in kind and not only in quantity and distinguishes the new preparation from the older lipophilic topical preparations of the prior art used for the same purpose.

The biphasic gel matrix cream unexpectedly causes a desirable slowed rate in percutaneous transfer of a pharmacologically active substance which effectively extends the desired bioavailability of the active substance from 1.5 to 3 times longer than occurs from the biphasic emulsion cream of the invention. This extended effect results from the new dimension of gel retardation of fluid diffusion across the epidermal-cream interface which in turn moderates the diffusion driving force.

It appears that the hydroxyalkylcellulose forms a colloidal gel at the hydrophilic-lipophilic emulsion interface which impedes the flow of colloid materials across the internal gel interface and retards the saturation of the respective barrier-reservoir equalibria in the epidermal layers. Thus molecules transported from the internal lipophilic phase to the external hydrophilic phase of the cream must first traverse the colloidal hydroxyalkylcellulose gel matrix formed at the interface of the two phases. The polar hydrogen bonding chelation centers of the hydroxyalkylcellulose polymer chain loosely hydrogen bond the charged molecules as they traverse the gel interface. When such hydrogen binding occurs, the diffusion of the molecules is interrupted. This type of loose hydrogen bonding is readily reversible, subject to displacement by a stronger polar charged moiety.

The loosely hydrogen bonded active molecule on the hydroxyalkylcellulose impede the transport of the molecules from the base to the skin through a reversal in the flow of skin-tissue fluids. The reverse flow of skin-tissue fluid brings salt ions of skin fluids into the gel matrix to aid in the displacement of the hydrogen bonded molecules from the hydroxyalkylcellulose gel surface, to re-establish transdermal flow patterns.

This control of the rate of diffusion of molecules from the biphasic gel matrix cream through hydrogen bonding impedance provides a means to obtain target drug action. Through the delayed sustained percutaneous transfer of the active ingredient, there is a longer period of tissue exposure to the traversing molecules through the skin pathways which provides an improved local biologic activity. The flow of active ingredient is slowed, but continuous, and in amounts sufficient to exert a local pharmacologic action but without the chemical ionic shock, toxic accumulations and drug degradation of the older preparations.

The preparations of the invention thereby provide a selective action with greater therapeutic flexibility. When a rapid bioavailability of an active compound is desired by percutaneous administration, then the biphasic lipophilic-hydrophilic emulsion cream of the invention is preferred. When a selective sustained local action to treat skin disease is desired, then the biphasic lipophilic-hydrophilic emulsion gel matrix cream is preferred. The respective preparations may also be used interchangeably so that the cream will be found advantageous to treat skin diseases when a more rapid buildup of active materials avoids a resistance to therapy, as for example when a germicide is used and it is necessary to avoid microbial resistance.

The cream gel matrix on the other hand permits a slowed delayed exposure of skin to a keratolytic agent for example which is desired to enable new tissue growth to take hold while debriding the older tissue. Similarly, a sustained amount of an analgesic drug or a vasodilatory agent may be desired for extended periods of therapy once a steady state equilibrium is established. The selection of the proper transdermal vehicle system will be determined by the therapeutic goal; the patient's need, and the nature of the specific active substance being transported percutaneously.

When it is intended to use the transdermal route to achieve an effective bioavailability of the pharmacologically active substance or to locally treat a skin disease, then the appropriate active compound is added to the selected formed cream preparations of the present invention. The active ingredient may be added either during the manufacture or after the formation of the cream and/or gel matrix cream. A non-polar lipophilic active substance may be preferably dissolved in the lipophilic phase during manufacture while a polar hydrophilic component would be added to the hydrophilic phase of the preparation during manufacture. Alternatively the active medicament may be incorporated by simple levigation directly into the cream vehicle and this method is preferred for the extemporaneous compounding of medicinals utilized in the pharmacy.

Among the preferred pharmacologically active substances which may be used for transdermal administration in the preparation of the present invention may be mentioned the following:

(a) Vasodilating agents such as organic and inorganic nitrite and nitrate compounds, nicotinic acid, nicotinic acid esters and nicotinyl alcohol; propanolol and isopropanol;

(b) Steroid compounds such as cortisone, betamethasone, dexamethasone, hydrocortisone, prednisolone, prednisone, methyl prednisolone, triamcinolone, flumethasone, flucinolone, fluxinanide, fluoromethalone and flurandrenolide.

(c) Analgesic compounds such as aspirin, salicylate esters, sodium salicylate, lithium salicylate, magnesium salicylate, choline salicylate, phenylbutazone, colchicine alkaloid and triethanolamine salicylate.

(d) Antimicrobial products such as polyvinylpyrrolidoneiodine, chlorhexidine, vioform, tetracycline and its salts, gentamicin and its salts, kanamycin and its salts, chloramphenicol and its salts and griseofluvin.

(e) Antihistamine compounds such as diphenhydramine hydrochloride, dimenhydrinate and its salts, carbinoxamine maleate, tripelennamine hydrochloride, pyrilamine maleate, antazoline phosphate, methapyrilene hydrochloride, chloropheniramine maleate, cyclizine hydrochloride, meclizine hydrochloride and promethazine hydrochloride.

(f) Histamine and its salts.

In use the preparation according to the invention may be applied to the skin surface in an amount which will be effective to meet the therapeutic needs of the patient. While the precise amount of the cream or the gel matrix cream to be applied to the skin will be influenced by the extend and severity of the disease process being treated, parameters may be adopted to suit the individual requirements as is known in the art.

The exact site for application of the preparation of the present invention is not critical, except that the skin surface should be such as to be conducive to transdermal penetration. Generally it will be found that the creams may be applied to the forearm, the abdomen and chest, the back, and the inner surface of the thighs. When a specific local response is intended, as for example the relief of pain of an inflamed shoulder or elbow, the appropriate preparation should be applied in close proximity to the affected organ site.

Blood samples obtained within one-half hour after application of the appropriate preparation reveals penetration of the active ingredient in the skin and blood. The improved bioavailability of the pharmacologically active substance is also apparent from its presence in the urine and faeces. Thus, within one-half hour after the application of the steroid containing creams of the invention, a positive identification test for the steroid in urine is obtained. Similarly, a positive identification test for salicylates in urine will be found within one-half hour after application of the salicylate containing cream. This rapid penetration does not occur when the same preparation, however without nitroglycerine, is used.

When nitroglycerine is used as the active ingredient to treat angina, the onset of effective vasodilation takes place within twenty minutes and rapidly achieves the steady state of bioavailability which persists for as long as six hours. Through the appropriate use of the gel matrix cream preparation of the invention, the duration of the effect may be increased to 10 to 12 hours. Individual patient differences may be manifested in the rate of absorption of the compound and consequent effects from both preparations.

DESCRIPTION OF PREFERRED EMBODIMENTS

The following examples are given to illustrate the invention. The scope of the invention is not, however, meant to be limited to the examples.

EXAMPLE 1

A biphasic cream emulsion preparation of the present invention was made as follows:

| Ingredient | Amount |
|---|---|
| 10% Adsorbate of Nitroglycerine on Lactose, which is known in the trade as S.D.M. No. 16 | 10 g |
| A Mixture of 90 parts Cetostearyl Alcohol + 10 parts sodium alkyl sulphate, which is known in the trade as Dehydag Wax SX | 20 g |
| Oleic Acid Decyl Ester, which is known in the trade as Cetiol V | 10 g |
| A Mixture of Sorbitan Mono-Oleate 28 parts and Polyoxyethylene Mono-Oleate 72 parts, which is known in the trade as HLB 12 Emulsifier | 5 g |
| Combination of ester of p-aminobenzoic acid, which is known in the trade as Nipastat | 2 g |
| Water, q.s. | to 100 g |

The Dehydag Wax SX, Cetiol V, HLB 12 emulsifier and Nipastat are mixed together. The mixture is heated to 80° C. with constant stirring to produce a homogeneous liquid system. The S.D.M. No. 16 is stirred in.

The water, preheated to 80° C., is added and the system cooled under conditions of constant agitation to produce a soft white homogeneous cream which is packaged in appropriate containers.

This cream emulsion is effective in the treatment of angina.

It will be appreciated that in the formulation of Example 1 various changes may be made in components and ranges; for example:

Dehydag Wax SX=10−25% w/w.

Certiol V=5−15%. Also Cetiol V can be replaced by any non-irritant oil with a structure similar in nature to skin lipids/sebum, for example isopropyl myristate or isopropyl palmitate.

The HLB 12 emulsifier system can be varied to read from HLB 8 system to HLB 14 system. The percentage inclusion can be from 1-20%.

Of course the water content can be varied according to the percentage inclusions of the components mentioned.

EXAMPLE 2

The procedure of Example 1 was followed but only 2.5 g of S.D.M. No. 16 was used. This preparation can be used as a carrier for other medicaments.

EXAMPLE 3

The procedure of Example 1 was used but only 0.5 g of S.D.M. No. 16 was used. This preparation can be used as a carrier for other medicaments.

EXAMPLE 4

A biphasic emulsion gel matrix cream was prepared as follows:

Step 1: 6 ml of Deionized water was dissolved in 0.1 gm. of maleic acid and 2 gm. of hydroxypropylcellulose were added. The mixture was stirred to obtain a uniform dispersion.

Step 2: In a separate vessel, 4 gm. of Emulsifying Wax, a waxy solid prepared from cetostearyl alcohol and a polyoxyethylene derivative of a fatty acid ester of sorbitan was melted. (Emulsifying Wax is available as an article of commerce and is a well defined pharmaceutical aid, with a melting range between 48° and 52° C.; the pH of 3 percent aqueous dispersion of Emulsifying Wax is between pH 7.0; the saponification number is not more than 14; the hydroxyl value is between 178 and 192 and the iodine value is not more than 3.5.)

Step 3: The melted Emulsifying Wax was added (with stirring) to the hydrated hydroxypropylcellulose gel of Step 1.

Step 4: 77 gm of Propylene glycol and 10 gm. of a 10 percent by weight mixture of nitroglycerine in lactose were placed in a third vessel. The nitroglycerine/lactose mixture comprised one part by weight of nitroglycerine and nine parts by weight of lactose and is available as an article of commerce. The mixture was stirred until dissolved.

Step 5: The nitroglycerine (lactose) solution in propylene glycol of Step 4 was added to the hydrated hydroxypropylcellulose and Emulsifying Wax of Step 3, with stirring to form a uniform emulsion gel matrix cream. The resultant gel matrix cream is packaged into appropriate containers of suitable size and shape.

EXAMPLE 5

In place of the hydroxypropylcellulose used in Example 4, above, there were substituted in equal amounts by weight hydroxymethylcellulose, hydroxyethylcellulose, and hydroxybutylcellulose, the remainder of the steps being the same. The cream gel matrix formed containing these agents had the same properties as described for the product of Example 4.

The hydroxyalkylcellulose is used in the critical ratio of from 1 part by weight of the selected hydroxyalkyl cellulose compound for each 2 to 4 parts by weight of the lipophilic phase present in the cream product. The hydroxyalkylcellulose component is preferably dispersed in the hydrophilic phase, prior to emulsification of the lipid phase.

EXAMPLE 6

In order to demonstrate the role of the hydroxyalkylcellulose component in delaying the rate of drug transfer from the biphasic emulsion cream systems of the invention, a conventional transfer cell apparatus was used and a comparison was made between the transfer rates of an indicator ingredient, as for example, nitroglycerine, from the respective creams obtained as a result of Examples 1 and 4. The conventional transfer cell apparatus comprised two cells in a glass container separated by a 5 micron milipore filter.

When conducting the diffusion comparison assay, an accurately weighed quantity of the test cream was loaded into one of the cells so that a uniform contact of the text cream with the cell barrier was achieved. The cell on the other side of the divisional barrier was filled with physiologic saline solution to provide the same osmotic pressure as skin. The transfer cell was then incubated in a controlled temperature oven set at 37° C. and an aliquot sample of the saline solution was removed periodically to determine the diffusion concentration of the indicator substance in the solution. The volume of saline solution removed for analysis was replaced to maintain a constant volume.

An accurately weighed sample of 2 grams of the formed cream preparation of Example 1, containing 1% nitroglycerine, was placed into one cell of a transfer cell apparatus and physiological saline solution in the other. In a second transfer cell apparatus, an accurately weighed sample of the formed cream of Example 4, containing 1% of nitroglycerine, was similarly placed into one cell of the apparatus and physiological saline solution in the other. Both transfer cells were then incubated in an oven at 37° C. and a 1 ml. aliquot sample of the saline solution was withdrawn at designated intervals over a six hour period. The amount of nitroglycerine in solution was determined spectrophotometrically and the results of the assay are as follows:

THE RELEASE* OF NITROGLYCERINE FROM THE EMULSION CREAMS

| Incubation Time | TEST PRODUCTS | |
|---|---|---|
| | Example 1 | Example 4 |
| After 15 minutes | 26% | 18% |
| After 30 minutes | 48% | 26% |
| After 1 hour | 72% | 33% |
| After 2 hours | 83% | 47% |
| After 4 hours | 93% | 68% |
| After 5 hours | 96% | 81% |
| After 6 hours | 95% | 94% |

*The values shown are the fraction amount of nitroglycerine diffused into the saline solution as a proportion of the total amount of starting 1% (w/w) nitroglycerine content present in the respective cream.

The diffusion of nitroglycerine from the product of Example 1 reached its equilibrium steady state between 2 hours and 4 hours, whereas no equilibrium was established during the 6 hour incubation period for the product of Example 4.

In another test utilizing the same technique, it was found that the product of Example 4 impeded the flow of the salicylate ion so that equilibrium was reached approximately 1.5 times slower than that for the product of Example 1.

When hydrocortisone was used as an indicator drug component, the diffusion impedance value for the product of Example 4 was 2.8 times the diffusion rate of hydrocortisone for the product of Example 1.

These test results establish that the cellulose component impedes the rate of release of an active ingredient from the biphasic emulsion cream by a factor of about 1.5–3.0. In view of this it can be expected that a single application to skin of the product of Example 4 would provide an active ingredient for percutaneous absorption over a period of about twice the duration as would be the product of Example 1.

EXAMPLE 7

To the product of Example 2, there was added the following nitrate and nitrite compounds viz amyl nitrite, sodium nitrite, erythrityl tetranitrate, pentaerythritol tetranitrate, isosorbide dinitrate, mannitol hexanitrate, trolnitrate phosphate in an amount of from 0.25% to 1.5% by weight a preferred concentration of approximately 1% by weight. The method of preparation was the same as that in Example 2. Example 4 may also be modified by using 2.5 g of S.D.M. No. 16 together with the amount of other nitrate or nitrite indicated above.

When these nitrate and nitrite compounds are administered percutaneously, their appearance in blood will be observed within one-half hour and within approximately the same time, the urine will give a positive identification test for the particular active substances used.

EXAMPLE 8

The following analgesic compounds were incorporated into the creams obtained according to Example 2 and Example 4 modified by using 2.5 g of S.D.M. No. 16.

| Compound | Concentration Range (% by weight) |
|---|---|
| Aspirin | 5–15% |
| Methyl salicylate | 1–10% |
| Sodium salicylate | 5–15% |
| Potassium salicylate | 5–15% |
| Lithium salicylate | 5–15% |
| Magnesium salicylate | 5–15% |
| Choline salicylate | 5–15% |
| Triethanolomine salicylate | 5–15% |
| Phenylbutazone | 5–15% |
| Colchicine alkaloid | 1–5% |
| Triethanolamine salicylate | 5–15% |

The selective active substance were incorporated in the formed products of the Examples referred to or were added to the lipophilic and/or hydrophilic phases during the manufacture of the respective creams. The finished products were stable and provided both a local as well as a systemic analgesic action.

When these products were applied to the skin of the abdomen, thigh, or the back, from 1 to 6 times daily, an effective bioavailability resulted. The active moiety could be determined in blood within 30 minutes after administration and a positive urine test could be observed 30 to 40 minutes after application to the skin.

When the above products were tested in accord with the method of Example 6, it was found that the analgesic preparation prepared in accord with Example 4 modified by the use of 2.5 g S.D.M. No. 16, diffused the active ingredient by a factor of between 1 and 2 times slower than the diffusion of the product prepared in accord with the method of Example 2.

EXAMPLE 9

A steroid active ingredient could be administered percutaneously by incorporation into the creams of Example 2 and Example 4, modified by the use of 2.5 g of S.D. No. 16, of the active compounds listed below in the concentrations mentioned. Such creams can be applied to the skin from 1 to 6 times daily.

| Steroid Compound | Concentration |
|---|---|
| Cortisone | 0.5–1.5% |
| Hetamethasone | 0.01–0.1% |
| Dexamethasone | 0.05–0.1% |
| Nydrocortisone | 0.1–2.0% |
| Prednisolone | 0.1–1.0% |
| Prednisone | 0.25–1.0% |
| Methyl prednisolone | 0.25–1.0% |
| Triamcinolone | 0.025–0.5% |
| Flumethosone | 0.025–0.1% |
| Flucinolone | 0.01–0.2% |
| Flucinanide | 0.025–0.1% |
| Fluoromethalone | 0.01–0.05% |

| Steroid Compound | Concentration |
| --- | --- |
| Flurandrenolide | 0.01–0.05% |

The steroid compound was preferably added to the lipophilic phase during the manufacturing of the appropriate cream vehicle although, on occasion, it was necessary to disperse the selected steroid compound in the hydrophilic phase or even to incorporate it directly into the finished cream. A systemic blood level of the respective steroid compound may be achieved via the transdermal route by the application of the preparation over a wide body area as for example, the abdomen or back. The appearance of the appropriate steroid in the blood occurs within 15 minutes after application to the skin.

As a class, the steroid cream preparations tested in accord with the method of Example 6 showed an impeded diffusion rate when used in the cream of Example 4, modified by the use of 2.5 g of S.D.M. No. 16 of from 1.5 to 3 times the diffusion rate from the cream of Example 2.

EXAMPLE 10

In order to administer an antimicrobial agent percutaneously to increase its blood level or to treat a skin infection, any one of the following compounds may be incorporated in the concentration set forth into the creams of Example 2 or Example 4 modified by the use of 2.5 g of S.D.M. No. 16.

It is understood that the antimicrobial agents listed have certain specific activities and generally recognized actions, some of which do not include a systemic use. For example, polyvinylpyrrolidone-iodine and vioform are antimicrobial agents which are generally not used systemically, but rather to exert a local germicidal action, whereas chloroamphenicol, tetracycline and gentamicin are used both topically and systemically. On the other hand, griseofulvin, is an antimicrobial agent which is administered systemically to achieve a local effect. Thus, the use of antimicrobial products in combination with the creams referred to above provides improved transdermal activity but does not in any way modify the recognized clinical applications for these products.

The improved efficacy of the antimicrobial creams of the invention is readily demonstrated by an increased epidermal tissue concentration of the respective agent which ranges from 2–6 times the amount penetrating into the tissue than when the older prior art preparations containing the same agent are used for the same purpose.

The antimicrobial products preferred to treat skin disease and/or to achieve an increased blood level are:

| Compound | Concentration (by weight) |
| --- | --- |
| Polyvinylpyrrolidone-iodine | 0.5–10.0% |
| Chlorhexidine | 0.5–10.0% |
| Vioform | 0.5–10.0% |
| Tetracycline (and its salts) | 0.5–10.0% |
| Gentamicin (and its salts) | 0.5–10.0% |
| Kanamycin (and its salts) | 0.5–10.0% |
| Chloramphenicol (and its salts) | 0.5–10.0% |
| Griseofulvin | 0.5–10.0% |

The selected active antimicrobial substance may be incorporated into the lipophilic or hydrophilic phases during manufacturing of the respective creams or to the formed creams by levigation. The preparations can be applied to the skin from 1–6 times daily in accord with the patients need, and the extent of the disease process being treated.

EXAMPLE 11

An antihistamine compound may be administered percutaneously, by incorporation into the creams of Example 2 or 4 (modified by the use of 2.5 g of S.D.M. No. 16). Suitable antihistamine compounds and use concentrations are given below:

| Compound | Concentration |
| --- | --- |
| Diphenhydramine hydrochloride | 0.5–2.0% |
| Dimenhydrinate (and its salts) | 0.5–2.0% |
| Carbinoxamine maleate | 0.5–2.0% |
| Tripelennamine hydrochloride | 0.5–2.0% |
| Pyrilamine maleate | 0.5–2.0% |
| Antazoline phosphate | 0.5–2.0% |
| Methapyrilene hydrochloride | 0.5–2.0% |
| Chlorpheniramine maleate | 0.5–2.0% |
| Cyclizine hydrochloride | 0.5–2.0% |
| Meclizine hydrochloride | 0.5–2.0% |
| Promethazine hydrochloride | 0.5–2.0% |

The antihistamine cream preparations are applied to the skin from 1–6 times daily.

EXAMPLE 12

For the treatment of peripheral microcirculatory disease involving the capillary bed and also ganglion neuralgias such as trigeminal neuralgia and Meniere's disease, the cream of Example 2 or Example 4 (modified by using 2.5 g of S.D.M. No. 16) containing trichloroethylene, 0.05–1.0% (by weight) and histamine 0.01–0.1% (by weight) as active ingredients, may be applied from 1 to 6 times daily.

The trichloroethylene and the histamine are preferably added to the lipophilic phase during manufacturing of the cream. However, if a histamine salt is preferred then this should be added to the hydrophilic phase during manufacture. The emulsion creams are stable, but because of the volatile character of trichloroethylene should be packaged in tight containers.

The diffusion of the histamine moiety from the product prepared in accord with Example 4 (modified as described) is three times greater than from the product of Example 2, and the concentration of histamine in the epidermal tissues is twice the amount appearing after the cream prepared in accord with Example 2. In contrast, however, the bioavailability of trichloroethylen is from 2–4 times greater with the produce prepared in accord with Example 2 than with the product of Example 4 (as modified).

In use, when a peripheral microcirculatory disease is being treated, the cream is applied from 4–6 times daily to the affected peripheral site. When a ganglionic neuralgia is being treated, then the cream is applied to the abdomen or forearm or back from 1–6 times daily.

The exact dosage to be administered will depend on the severity of the disease and the dosage guidelines known to the art should be followed. A beneficial response will usually be observed within 10 days after the initiation of treatment. On occasion, it will be found that a tolerance to the active ingredients will occur in which case therapy should be stopped but it may be reinstituted after an appropriate waiting period.

While the invention has been illustrated with specific compositions and specific proportions, it is apparent that variations and modifications thereof can be made.

What is claimed is:

1. Composition for the percutaneous administration of a specifically acting medicament suitable for transdermal administration, said medicament being a steroid, analgesic, antimicrobial agent, antihistamine or histamine, said composition comprising a physiologically compatible biphasic lipophilic/hydrophilic carrier having a hydrophilic/lipophilic balance value of 8-14 and having said medicament distributed therein in a transdermal administration effective amount for the specific action of said medicament, and also having distributed therein nitroglycerine in an amount sufficient to cause local vasodilation to promote the percutaneous absorption of said medicament but insufficient to cause adsorption of the nitroglycerine into the blood.

2. Composition according to claim 1 wherein the hydrophilic component of said carrier is water, propylene glycol or glycerine and wherein the lipophilic component is a higher aliphatic alcohol or an ester thereof.

3. Composition according to claim 1 wherein said carrier includes emulsifiers to provide said hydrophilic/lipophilic balance.

4. Composition according to claim 1 wherein said carrier is in the form of a cream base.

5. Composition according to claim 1 and also including a hydroxyloweralkylcellulose in the carrier.

6. Composition according to claim 1 wherein said medicament is a steroid.

7. Composition according to claim 6 wherein said steroid is cortisone, beamethasone, dexamethasone, hydrocortisone, prednisolone, prednisone, methyl prednisolone, triamcinolone, flumethasone, flucinolone, fluxinanide, fluoromethalone or flurandrenolide.

8. Composition according to claim 1 wherein said medicament is an analgesic.

9. Composition according to claim 8 wherein said analgesic is aspirin, salicylate esters, sodium salicylate, lithium salicylate, magnesium salicylate, choline salicylate, phenylbutazone, colchicine alkaloid or triethanolamine salicylate.

10. Composition according to claim 1 wherein said medicament is an antimicrobial agent.

11. Composition according to claim 10 wherein said antimicrobial agent is polyvinylpyrrolidone-iodine, chlorhexidine, viform, tetracycline, tetracycline salts, gentamicin, gentamicin salts, kanamycin, kanamycin salts, chloramphenicol, chloramphenicol salts, or griseofluvin.

12. Composition according to claim 1 wherein said medicament is an antihistamine.

13. Composition according to claim 12 wherein said antihistamine is diphenylhydramine hydrocholoride, dimenhydrinate, dimenhydrinate salts, carbinoxamine maleste, tripelennamine hydrochloride, pyrilamine maleate, antazoline phosphate, methapyrilene hydrochloride, chloropheniramine maleate, cyclizine hydrochloride, meclizine hydrochloride or promethazine hydrochloride.

14. Composition according to claim 1 wherein said medicament is histamine or a salt thereof.

15. Composition according to claim 1 wherein the amount of said nitroglycerine is between about 0.05% by weight and 0.25% by weight.

16. Method of achieving percutaneous administration of a specifically acting medicament suitable for transdermal administration, said medicament being a steroid, analgesic, antimicrobial agent, antihistamine or histamine, which comprises topically applying a specifically acting effective amount of the composition of claim 1 to a patient requiring the specific action of said medicament.

17. Method according to claim 16 wherein the effective amount of said nitroglycerine is between about 0.05% by weight and 0.25% by weight.

18. Method of producing the composition of claim 1, which comprises dispersing said nitorglycerine in a lipophilic phase of a higher aliphatic alcohol of 8-18 carbon atoms, mixing the resultant lipophilic phase containing nitroglycerine with a hydrophilic phase of water, propylene glycol or glycerine and with said effective amount of said medicament, and emulsifying the thus obtained mixture.

19. Method according to claim 18 wherein said aliphatic alcohol is substituted by a further aliphatic group containing 8-18 carbon atoms.

20. Method according to claim 18 wherein said nitroglycerine is dispersed in the form of a lactose adsorbate.

21. Method according to claim 18 wherein the emulsion is modified with hydroxyloweralkylcellulose.

22. Method according to claim 21 wherein the amount of said hydroxyloweralkylcellulose is one part by weight per each 2-4 parts by weight of said higher aliphatic alcohol.

* * * * *